United States Patent [19]

Kolber

[11] Patent Number: 5,205,818

[45] Date of Patent: Apr. 27, 1993

[54] PATENCY MAINTENANCE SYSTEM

[75] Inventor: Chris M. Kolber, Nashua, N.H.

[73] Assignee: Abbott Laboratories, Abbott Park, Ill.

[21] Appl. No.: 635,456

[22] Filed: Dec. 28, 1990

[51] Int. Cl.⁵ .............................................. A61M 31/00
[52] U.S. Cl. ...................................... 604/53; 604/131; 604/269
[58] Field of Search ............................ 604/80, 246–247, 604/257, 266, 269, 131, 151, 53; 128/DIG. 12

[56] References Cited

U.S. PATENT DOCUMENTS

| | | | |
|---|---|---|---|
| 3,916,892 | 11/1975 | Latham, Jr. ........................ | 604/269 X |
| 4,496,343 | 1/1985 | Prosl et al. ............................ | 604/86 |
| 4,497,468 | 2/1985 | Hubbard et al. ................. | 604/249 X |
| 4,601,697 | 7/1986 | Mammolenti et al. ............... | 604/43 |
| 4,867,743 | 9/1989 | Vaillancourt ........................ | 604/135 |
| 4,976,697 | 12/1990 | Walder et al. ........................ | 604/164 |

Primary Examiner—C. Fred Rosenbaum
Assistant Examiner—C. Maglione
Attorney, Agent, or Firm—A. Nicholas Trausch; Thomas M. Breininger

[57] ABSTRACT

A method and apparatus for maintaining the patency of a vein access device in which a dilute solution of an anticoagulant drug is slowly infused into the vein access device. The patency device includes a self-energized container and means for adding a medicament without disconnecting the patency device from the vein access device. In accordance with a preferred embodiment, a self-energized container delivers a heparin solution to the vein access device at a concentration from about 0.01 to about 0.99 international heparin units per milli-. liter of diluent at a flow rate from about 0.01 to about 1.0 milliliters per hour.

6 Claims, 1 Drawing Sheet

PATENCY MAINTENANCE SYSTEM

BACKGROUND OF THE INVENTION

1. Field Of The Invention

This invention generally relates to a method and apparatus for maintaining the patency of an indwelling vein access device and, more particularly, to such a method and apparatus that utilizes a self-energized container to slowly infuse a dilute solution of an anticoagulant drug, such as heparin, into a vein access device and which permits the adding of a medicament without disconnecting the container from the vein access device.

2. Description Of The Prior Art

There are numerous approaches to patency maintenance currently being utilized in venipuncture practice. The most common approaches are the heparin lock procedure and the KVO procedure.

In the KVO procedure a KVO solution (generally a saline solution) is slowly directed through the vein access device (IV catheter) into the patient at a flow rate generally from about 1 ml/hour to about 10 ml/hour. While this procedure seems to maintain the patency of the vein access device, it has the disadvantage of infusing a large volume of fluid into the patient and it limits the mobility of the patient.

In the widely used heparin lock procedure, a concentrated heparin solution is contained in a capped off segment of tubing in fluid communication with the vein access device. The concentration of the heparin is generally from about 10 to about 100 international heparin units per milliliter of diluent. At these concentrations of heparin, it is necessary to initiate a flush procedure of the heparin lock device and vein access device prior to infusion of most antibiotic drugs through the vein access device, in order to avoid contamination resulting from the incompatibility of the drug with the heparin. Most heparin lock devices utilize the cumbersome SASH procedure in which (a) the device is flushed with a bolus dose of saline solution, (b) the medicament or drug is infused into the device, (c) the device is again flushed with a bolus dose of saline solution, and (d) the device is filled with the concentrated solution of heparin. While this procedure is widely regarded as effective to maintain patency of the vein access device, it is generally regarded as being time consuming and costly.

There is a need for a method and apparatus for reliably maintaining the patency of a vein access device in a manner that minimizes manipulative steps, is economical, minimizes the volume of fluid that is infused into the patient, and does not inhibit patient mobility.

SUMMARY OF THE INVENTION

Briefly stated, the invention provides a method and apparatus for maintaining the patency of a vein access device in which a dilute solution of an anticoagulant drug, such as heparin, is slowly infused into the vein access device. The patency device is preferably self-energized and includes a means for adding a medicament without disconnecting the patency device from the vein access device.

In accordance with a preferred embodiment of the invention, the patency device includes a self-energized container that contains a dilute solution of heparin. The self-energized container delivers the heparin solution to the vein access at a substantially constant low flow rate. The concentration of the heparin solution is preferably from about 0.01 to about 0.99 international heparin units per milliliter of diluent and the flow rate is preferably from about 0.01 to about 1.0 milliliters per hour.

The term "self-energized container", as used herein, is intended to include a wide range of known self-powered, compact pump devices that (a) include a container for storing a fluid and means for dispensing such fluid from the container at a controlled flow rate over a prolonged period of time, (b) do not require electricity or gravity to operate and (c) are wearable by the patient. Such devices may include, but are not limited to the following: osmotic infusion pumps; elastomeric membrane or bladder infusion pumps; vapor pressure delivery pumps; hydrogel driven osmotic pumps; and the like. Exemplary of such pump devices are those disclosed in U.S. Pat. Nos. 4,692,151, 4,769,008, 4,838,862, 4,898,582, 4,410,328, 4,318,400, 4,419,096, 3,840,009, 4,223,061 and 4,203,440.

The patency device includes an access site for directing a medicament or drug into the vein access device. A check valve is provided to preclude the medicament or drug from mixing with the heparin solution in the self-energized container.

The invention, both as to its method of operation and apparatus, will be best understood from the following description of specific embodiments when read in connection with the accompanying drawings.

DESCRIPTION OF PREFERRED EMBODIMENTS

In accordance with the method of the present invention, the patency of a vein access device, such as a catheter, is maintained by continuously delivering a dilute solution to an anticoagulant drug at a low flow rate to the vein access device. The anticoagulant drug may include heparin, urokinase, dextran, or the like. The delivery of such solution maintains the patency of the vein access device in a manner that minimizes the volume of fluid directed into the patient and the potential adverse effects associated therewith. The low concentration of the anticoagulant drug also reduces the risks associated with the incompatibility of the drug with certain antibiotics.

The anticoagulant drug is preferably a heparin solution having a concentration from about 0.01 to about 0.99 international heparin units per milliliter of diluent, most preferably at the lower end of said range. The heparin solution is preferably delivered to the vein access device at a flow rate from about 0.01 to about 1.0 milliliters per hour, most preferably at the lower end of said range.

Figure 3:
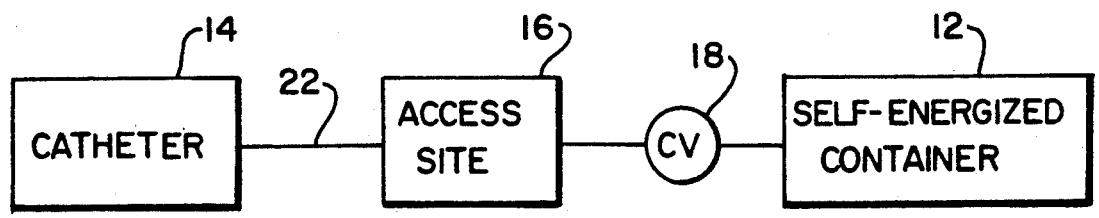
FIG. 3 is a schematic representation depicting the components in accordance with the invention.

Referring to FIG. 3, a schematic representation of a patency device 10, in accordance with the broad concepts of the invention, is shown as including a self-energized container 12 for directing a heparin solution to a catheter 14 at the concentration and flow rate as disclosed hereinabove. An access site 16 is preferably interposed between the container 12 and the catheter 14 to infuse a medicament or drug into the catheter. A check valve 18 is preferably interposed between the access site 16 and the container 12 to preclude the medicament or drug from mixing with the heparin solution in the container.

Figure 1:
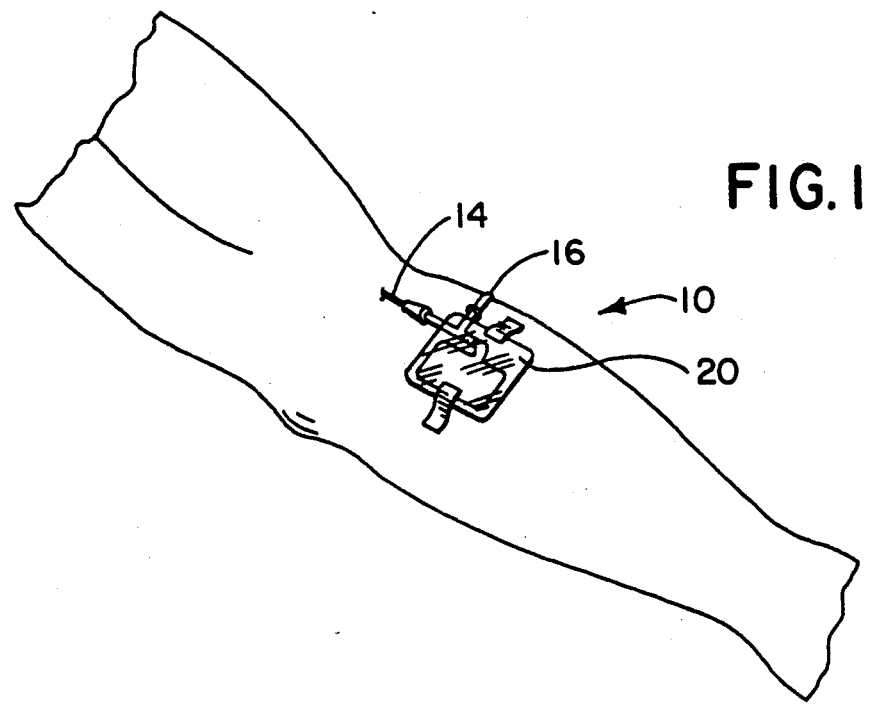
FIG. 1 is a perspective view of a preferred embodiment of a patency device in accordance with the invention during use.
Figure 2:
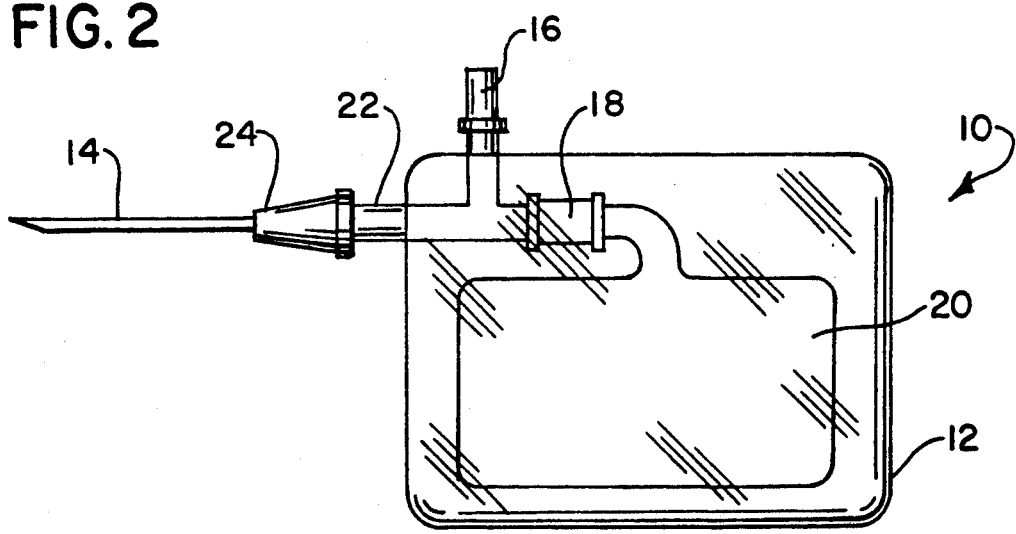
FIG. 2 is an enlarged elevational view of the patency device shown in FIG. 1.

Referring to FIGS. 1 and 2, patency device 10 includes a self-energized container 12 having a reservoir 20 that contains a dilute heparin solution having a concentration from about 0.01 to about 0.99 international heparin units per milliliter of diluent. The container 12 is designed to deliver the heparin solution from the reservoir 20 at a flow rate from about 0.01 to about 1.0 milliliters per hour.

The device includes an outlet line 22 for directing the heparin solution from container 12 to catheter 14 or other vein access device. Catheter 14 and outlet line 22 are provided with suitable luer connectors 24 to facilitate connection of the catheter to the outlet line.

In accordance with the invention, a suitable access site 16 is provided in communication with outlet line 22 to selectively infuse a medicament or drug into the catheter without disconnecting the self-energized container from the catheter. A suitable check valve 18 is positioned in outlet line 22 between access site 16 and the reservoir 20 to prevent the back flow of the drug into the heparin reservoir.

As best seen in FIG. 1, the patency device 10 may be secured to the patient's arm or elsewhere by tape or other suitable means. The device is sufficiently small in size to facilitate mobility of the patient. The device preferably includes a sufficient supply of heparin solution to last about 1 to 2 days. Should it become necessary, the self-energized container may be replaced without removal of the catheter from the vein of the patient by disconnecting the container at the luer connection.

The specific type and construction of the self-energized container 12 does not form a part of the invention. As alluded to hereinabove, there are many such devices well known in the art that may be utilized to deliver the dilute heparin solution at the disclosed flow rates.

The patency device 10 is compact, portable and does not require much manipulation during use, which makes it particularly ideal for use by home care patients. The dilute nature and the low flow rate of the heparin solution avoids the necessity of saline flushes to avoid contamination with drugs and minimizes the quantity of fluid that is infused into the patient. The provision of the access site permits infusion of a medicament or drug into the patient without disconnecting the device.

Although the invention has been described in terms of certain preferred embodiments, other embodiments that are apparent to those of ordinary skill in the art are also within the scope of the invention. Accordingly, the scope of the invention is entitled to be defined in accordance with the spirit and scope of the appended claims.

What is claimed is:

1. A method for maintaining the patency of an indwelling vein access device, comprising the step of delivering a heparin solution to the vein access device having a concentration from about 0.01 to about 0.99 international heparin units per milliliter of diluent and a flow rate from about 0.01 to about 1.0 milliliters per hour.

2. The method as defined in claim 1 wherein the heparin solution is delivered from a self-energized container.

3. A method for maintaining the patency of an indwelling vein access device, comprising the sep of delivering a dilute solution of an inticoagulant drug from a self-energized container into the vein access device at a flow rate from about 0.1 to about 1.0 milliliters per hour.

4. Apparatus for maintaining the patency of an indwelling vein access device, comprising:
    (a) a vein access device;
    (b) self-energized container means containing a dilute solution of an anticoagulant drug comprising heparin solution having a concentration from about 0.01 to about 0.99 international heparin units per milliliter of diluent in fluid communication with said vein access device for delivering said solution to said vein access device at a low flow rate from about 0.01 to about 1.0 milliliters per hour;
    (c) an access site disposed between said container means and said vein access device in fluid communication therewith for directing a medicament into said vein access device; and
    (d) a check valve disposed between said access site and said container means in fluid communication therewith for preventing medicament directed into said access device through said access site from flowing into said container means.

5. The apparatus as defined in claim 4 wherein said vein access device is a catheter.

6. The apparatus as defined in claim 4 wherein said self-energized container means is small enough to be releasably attached to a patient's arm.

* * * * *

UNITED STATES PATENT AND TRADEMARK OFFICE
CERTIFICATE OF CORRECTION

PATENT NO. : 5,205,818
DATED : April 27, 1993
INVENTOR(S) : Chris M. Kolber

It is certified that error appears in the above-identified patent and that said Letters Patent is hereby corrected as shown below:

Column 4, line 19, replace "sep" with --step--
Column 4, line 20, replace "inticoagulant" with --anticoagulant--
Column 4, line 22, replace "0.1" with --0.01--

Signed and Sealed this

Fifteenth Day of March, 1994

Attest:

BRUCE LEHMAN

Attesting Officer

Commissioner of Patents and Trademarks